(12) United States Patent
Becker et al.

(10) Patent No.: US 7,235,243 B2
(45) Date of Patent: Jun. 26, 2007

(54) IMMUNOLOGICAL COMBINATION COMPOSITIONS AND METHODS

(75) Inventors: Robert S. Becker, Henryville, PA (US); Robert C. Huebner, Stroudsburg, PA (US); Maryann Gray, Bartonsville, PA (US); Karen S. Biscardi, South Sterling, PA (US); Lorne F. Erdile, Tassin la Demi Lune (FR); Bruno Guy, Lyons (FR)

(73) Assignee: Connaught Laboratories, Inc., Swiftwater, PA (US)

( * ) Notice: Subject to any disclaimer, the term of this patent is extended or adjusted under 35 U.S.C. 154(b) by 0 days.

(21) Appl. No.: 11/173,364

(22) Filed: Jul. 1, 2005

(65) Prior Publication Data

US 2006/0110408 A1    May 25, 2006

Related U.S. Application Data

(60) Division of application No. 10/096,687, filed on Mar. 12, 2002, now Pat. No. 6,984,385, which is a continuation of application No. 08/588,621, filed on Jan. 19, 1996, now Pat. No. 6,379,675, which is a continuation-in-part of application No. 08/476,656, filed on Jun. 7, 1995, now Pat. No. 6,251,405.

(51) Int. Cl.
*A61K 39/00* (2006.01)

(52) U.S. Cl. .............................. 424/192.1; 424/193.1; 424/197.11; 424/200.1; 424/201.1; 424/203.1; 424/234.1; 424/237.1; 424/244.1; 435/69.1; 435/69.3; 435/69.7; 435/71.1; 530/350

(58) Field of Classification Search ............. 424/192.1, 424/193.1, 197.11, 200.1, 201.1, 203.1, 234.1, 424/237.1, 244.1; 435/69.1, 69.3, 69.7, 71.1; 530/350
See application file for complete search history.

(56) References Cited

FOREIGN PATENT DOCUMENTS

WO       93/07897     *   4/1993

* cited by examiner

*Primary Examiner*—Jennifer E. Graser

(57) ABSTRACT

Immununological compositions and methods for making and using them. The compositions contain at least one antigen and at least one lipoprotein and optionally an adjuvant. The lipoprotein can itself be antigenic or immunogenic. The antigen can be influenza HA and the lipoprotein a recombinantly expressed product having an OspA leader for lipidation and PspA for the protein portion. The antigen can be OspC and the lipoprotein OspA. The components of the composition are co-administered. A potentiated immunological response is obtained by the compositions and methods.

11 Claims, 5 Drawing Sheets

IMMUNOLOGICAL COMBINATION COMPOSITIONS AND METHODS

REFERENCE TO RELATED APPLICATIONS

This application is divisional of application Ser. No. 10/096,687, filed Mar. 12, 2002. now U.S. Pat. No. 6,984, 385, which is a continuation of application Serial No. 08/588,621, filed Jan. 19, 1996, now U.S. Pat. No. 6,379, 675, which is a continuation-in-part of application Ser. No. 08/476,656, filed Jun. 7, 1995, now U.S. Pat. No. 6,251,405.

Reference, especially wit respect to recombinant Borrelia proteins, is made to each of applications Ser. No. 07/973, 338, filed Oct. 29, 1992 (abandoned); Ser. No. 08/373,455 (Rule 62 FWC of U.S. Ser. No. 07/973,338), filed Jan. 17, 1995 (abandoned); Ser. No. 07/888,765, filed May 27, 1992 (abandoned); Ser. No. 08/211,891, filed Oct. 16, 1992 (abandoned: national phase of PCT/US92/08697); and Ser. No. 07/779,048, flled Oct. 18, 1991 (abandoned). Reference, especially with respect to structural genes of pneumococcal proteins, epitopic regions thereof, and administration of pneumococcal proteins, is made to each of applications Ser. No. 07/656,773, filed Feb. 15, 1991 (abandoned); Ser. No. 07/835 698, filed Feb. 12, 1992 (abandoned) Ser. No. 08/072,065, filed Jun. 3, 1993 (abandoned); Ser. No. 08/072, 068, filed Jun. 3, 1993 (abandoned); Ser. No. 08/214,222 filed Mar. 17,1994. now U.S. Pat. No. 5,804,193; Ser. No. 08/214,164, filed Mar. 17, 1994, now U.S. Pat. No. 5,728, 387; Ser. No. 08/247,491, filed May 23, 1994. now U.S. Pat. No. 5,965,400; Ser. No. 08/048,896, filed Apr. 20, 1993 (abandoned); Ser. No. 08/246,636, filed May 20, 1994. now U.S. Pat. No. 5,965,141; Ser. No. 08/458,399 (continuation-in-part of application Ser. No. 08/246,636. filed Oct. 7, 1994. now US. Pat. No. 5,965,141) filed Jun. 2, 1995. now U.S. Pat. No. 6,231,870; Ser. No. 08/446,201 filed May 19, 1995, now U.S. Pat. No. 6,042,838; Ser. No. 08/312,949, filed Sep. 30, 1994. now US. Pat. No. 6,027,734. With respect to Expression of Lipoproteins, reference is made to application Ser. No. 08/475,781, filed Jun. 7, 1995 (abandoned). And, with respect to Compostions and Methods for Administering Borrelia Burgdorferi Antigens mucosally, e.g., orally, for simulating an immunological response, reference is made to Barbour et al., application Ser. No. 08/588,637, filed Jan. 19, 1996, now U.S. Pat. No. 7,094,391.

Each of the aforementioned applications is hereby incorporated herein by reference. Several documents are cited in the following text, and each is also hereby incorporated herein by reference.

FIELD OF THE INVENTION

The present invention relates to compositions for eliciting an immunological response in a host, animal or human, and methods for making and using the same. The invention further relates to such compositions and methods wherein the composition comprises an antigen and a lipoprotein adsorbed to an adjuvant. More preferably, the lipoprotein is also antigenic or immunogenic, and thus the composition can be a combination, multivalent or "cocktail" composition. Accordingly, the invention also relates to co-administration of at least one antigen and at least one lipoprotein in a composition which can include additional ingredients, such as an adjuvant.

The lipoprotein can be a naturally occurring lipoprotein or a recombinant lipoprotein. The recombinant lipoprotein can be from expression by a vector of homologous sequences for the lipidated and protein portions of the lipoprotein, i.e., the sequences for the lipidation and protein can naturally occur together. In such a recombinant lipoprotein, the lipidation thereof can be from expression of a first nucleic acid sequence and the protein thereof can be from expression of a second nucleic acid sequence, wherein the first and second nucleic acid sequences, which do not naturally occur together, and such sequences can be expressed as a contiguous lipoprotein. Thus, the invention relates to compositions and methods involving administration of lipoproteins, including recombinant lipoproteins; and the recombinant lipoproteins can be similar to native proteins, or novel hybrid proteins.

The invention further relates to the aforementioned compositions for eliciting an immunological response and methods for making and using the same wherein the lipoprotein is recombinantly expressed lipoprotein from expression of such aforementioned first and second nucleic acid sequences wherein the first nucleic acid sequence encodes a Borrelia lipoprotein leader sequence; preferably such a recombinant lipidated protein expressed using the nucleic acid sequence encoding the OspA leader sequence. In a preferred embodiment the lipoprotein can be OspA; and thus, the invention also relates to recombinant OspA and uses thereof the compositions and methods.

Several publications are referenced in this application. Full citation to these references is found at the end of the specification immediately preceding the claims or where the publication is mentioned; and each of these publications is hereby incorporated herein by reference.

BACKGROUND OF THE INVENTION

Immunogenicity can be significantly improved if an antigen is co-administered with an adjuvant, commonly used as 0.001% to 50% solution in phosphate buffered saline (PBS). Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune response to, for example, vaccines. Intrinsic adjuvants, such as lipopolysaccarides, normally are the components of the killed or attenuated bacteria used as vaccines. Extrinsic adjuvants are immunomodulators which are typically non-covalently linked to antigens and are formulated to enhance the host immune response. Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramoyl dipeptide (MDP) and lipopolysaccharide (LPS), as well as lipid A, and liposomes. To efficiently indvice humoral immune response (HIR) and cell-mediated immunity (CMI), immunogens are preferably emulsified in adjuvants.

Desirable characteristics of ideal adjuvants include any or all of:
 (1) lack of toxicity;
 (2) ability to stimulate a long-lasting immune response;
 (3) simplicity of manufacture and stability in long-term storage;
 (4) ability to elicit both CMI and HIR to antigens (5) administered by various routes;
 (5) synergy with other adjuvants;
 (6) capability of selectively interacting with populations of antigen presenting cells (APC);
 (7) ability to specifically elicit appropriate $T_H1$ or $T_H2$ cell-specific immune responses; and
 (8) ability to selectively increase appropriate antibody isotype levels (for example IgA) against antigens.

U.S. Pat. No. 4,855,283 granted to Lockhoff et al. on Aug. 8, 1989 which is incorporated herein by reference thereto teaches glycolipid analogs including N-glycosylamides, N-glycosylureas and N-glycosylcarbamates, each of which is substituted in the sugar residue by an amino acid, as immune-modulators or adjuvants. Thus, Lockhoff et al. (U.S. Pat. No. 4,855,283) reported that N-glycolipids analogs displaying structural similarities to the naturally occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugar through the anomeric carbon atom, to mimic the functions of the naturally occurring lipid residues.

U.S. Pat. No. 4,258,029 granted to Moloney, assigned to Connaught Laboratories Limited and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Octodecyl esters of aromatic amino acids complexed with a recombinant hepatitis B surface antigen, enhanced the host immune responses against hepatitis B virus.

Bessler et al., "Synthetic lipopeptides as novel adjuvants," in the 44th Forum In Immunology (1992) at page 548 et seq., especially at 548–550, incorporated herein by reference, is directed to employing lipopeptides as adjuvants when given in combination with an antigen. The lipopeptides typically had P3C as the lipidated moiety and up to only 5 amino acids, e.g., P3C-SG, P3C-SK4, P3C-SS, P3C-SSNA, P3C-SSNA. The lipopeptide was coupled with or added to only certain antigens or to non-immunogenic proteins, such as P3C-SSNA supplementing *S. typhimurium* vaccine, PC3-SS coupled to VP1(135–154) of foot-and-mouth disease, PC3-SG-OSu coupled to non-immunogenic protein hirudin, P3C-SK coupled to FITC or DNP or P3C-SG coupled to a metabolite from *Streptomyces venezuelae*. While adjuvant mixing and conjugating procedures of Bessler can be employed in the practice of the present invention, Bessler fails to teach or suggest employing a lipoprotein with at least one antigen in a composition, especially such compositions wherein the lipoprotein is also antigenic, or the immunological combination compositions and methods of this invention.

In this regard, a distinction between a peptide, especially a peptide having up to only about 5 amino acids, and a protein is being made, as is a distinction between an antigenic lipoprotein and a non-antigenic lipopeptide, inter alia. Peptides differ immunologically from proteins in that short peptides have the potential for direct presentation by the major histocompatibility complex (MHC), while proteins require processing prior to presentation to T-cells. A peptide further differs from a protein in that a protein is large enough that it is capable of forming functional domains (i.e., having tertiary structure), whereas a peptide cannot.

Nardelli et al. [Vaccine (1994), 12(14):1335–1339] covalently linked a tetravalent multiple antigen peptide containing a gp120 sequence to a lipid moiety and orally administered the resulting synthetic lipopeptide to mice. It was found that both mucosal IgA response and systemic plasma IgG were stimulated, and cell-mediated immunity, as shown by lymphokine production and generation of a specific cytotoxic response, was induced. Only a short peptide was used, rather than a whole lipoprotein, and there is no teaching or suggestion that the synthetic lipopeptide could be used as an adjuvant for other proteins. In fact, this reference actually teaches away from the use of lipoproteins, which are more soluble than lipopeptides, as immunogens; see, e.g. p. 1338, last line ("soluble proteins are not immunogens by oral routes").

Croft et al. [J. Immunol. (1991), 146(5): 793–796] have covalently coupled integral membrane proteins (Imps) isolated from *E. coli* to various antigens and obtained enhanced immune responses by intramuscular injection into mice and rabbits. However, there are disadvantages to coupling the lipoprotein and the antigen covalently. Important epitopes may be damaged, and the coupling procedure is difficult to control and often requires the use of toxic cross-linkers. Thus, it would be advantageous to provide a method for inducing an enhanced immunological response which does not require that the antigen be cross-linked to a protein. Moreover, when the antigen CSP-OVA was merely mixed, rather than covalently linked, with the lipoprotein TraT, only a small increase in antibody response was obtained. Croft et al. therefore concluded that the lipid is not necessary for the adjuvant effect, contrary to the surprising findings of the present inventors.

U.S. Pat. No. 4,439,425 relates to lipopeptides having 2 to 10 amino acids and their prophylactic administration by oral or rectal routes.

Bessler et al. ["Synthetic Lipopeptide Conjugates Constitute Efficient Novel Immunogens and Adjuvants in Parenteral and Oral Immunization" (Abstract), Meeting on Molecular Approaches to the Control of Infectious Diseases, (Sep. 13–17, 1995), Cold Spring, Harbor Laboratory (not prior art in view of Jun. 7, 1995 filing date of U.S. Ser. No. 08/476,656)] relates to the oral administration of lipopeptides having six amino acids which were covalently coupled to antigens. The lipopeptide-antigen conjugates were found to induce a hapten-specific immune response.

Schlecht et al. [*Zbl. Bakt.* (1989) 271:493–500] relates to *Salmonella typhimurium* vaccines supplemented with synthetically prepared derivatives of a bacterial lipoprotein having five amino acids. The vaccines were administered by two intraperitoneal injections and challenged intraperitoneally with graded doses of *S. typhimurium*. When the protective capacity of the supplemented vaccines was compared with that of the unsupplemented vaccine, it was found that 90% of the *S. typhimurium* vaccine could be replaced by the lipopeptide without a recognizable decrease in protective capacity.

Substantial effort has been directed toward the development of a vaccine for Lyme disease. Two distinct approaches have been used for vaccine development. One approach is to use a vaccine composed of whole inactivated spirochetes, as described by Johnson in U.S. Pat. No. 4,721,617. A whole inactivated vaccine has been shown to protect hamsters from challenge and has been licensed for use in dogs.

Due to the concerns about cross-reactive antigens within a whole cell preparation, human vaccine research has focused on the identification and development of non-cross-reactive protective antigens expressed by B. burgdorferi. Several candidate antigens have been identified to date. Much of this effort has focused on the most abundant outer surface protein of B. burgdorferi, namely outer surface protein A (OspA), as described in published PCT patent application WO 92/14488, assigned to the assignee hereof. Several versions of this protein have been shown to induce protective immunity in mouse, hamster and dog challenge studies. Clinical trials in humans have shown the formulations of OspA to be safe and immunogenic in humans [Keller et al., JAMA (1994) 271:1764–1768]. Indeed, one formulation containing recombinant lipidated OspA as described in the aforementioned WO 92/14488, is now undergoing Phase III safety/efficacy trials in humans.

While OspA is expressed in the vast majority of clinical isolates of B. burgdorferi from North America, a different picture has emerged from examination of the clinical Borrelia isolates in Europe. In Europe, Lyme disease is caused by three genospecies of Borrelia, namely B. burgdorferi, B. garinii and B. afzelii. In approximately half of the European isolates, OspA is not the most abundant outer surface protein. A second outer surface protein C (OspC) is the major surface antigen found on these spirochetes. In fact, a number of European clinical isolates that do not express OspA have been identified. Immunization of gerbils and mice with purified recombinant OspC produces protective immunity to B. burgdorferi strains expressing the homologous OspC protein [V. Preac-Mursic et al., INFECTION (1992) 20:342–349; W. S. Probert et al., INFECTION AND IMMUNITY (1994) 62:1920–1926]. The OspC protein is currently being considered as a possible component of a second generation Lyme vaccine formulation.

Recombinant proteins are promising vaccine or immunogenic composition candidates, because they can be produced at high yield and purity and manipulated to maximize desirable activities and minimize undesirable ones. However, because they can be poorly immunogenic, methods to enhance the immune response to recombinant proteins are important in the development of vaccines or immunogenic compositions. Moreover, it would be greatly desired to be able to administer such proteins in combination with other antigens.

A very promising immune stimulator is the lipid moiety N-palmitoyl-S-(2RS)-2,3-bis-(palmitoyloxy) propyl-cysteine, abbreviated Pam$_3$Cys. This moiety is found at the amino terminus of the bacterial lipoproteins which are synthesized with a signal sequence that specifies lipid attachment and cleavage by signal peptidase II. Synthetic peptides that by themselves are not immunogenic induce a strong antibody response when covalently coupled to Pam-jCys [Bessler et al. (1992)].

In addition to an antibody response, one often needs to induce a cellular immune response, particularly cytoxic T lymphocytes (CTLs). Pam$_3$Cys-coupled synthetic peptides are extremely potent inducers of CTLs, but no one has yet reported CTL induction by large recombinant lipoproteins.

The nucleic acid sequence and encoded amino acid sequence for OspA are known for several B. burgdorferi clinical isolates and is described, for example, in published PCT application WO 90/04411 (Symbicom AB) for B31 strain of B. burgdorferi and in Johnson et al., Infect. Immun. 60:1845–1853 for a comparison of the ospA operons of three B. burgdorferi isolates of different geographic origins, namely B31, ACA1 and Ip90.

As described in WO 90/04411, an analysis of the DNA sequence for the B31 strain shows that the OspA is encoded by an open reading frame of 819 nucleotides starting at position 151 of the DNA sequence and terminating at position 970 of the DNA sequence (see FIG. 1 therein). The first sixteen amino acid residues of OspA constitute a hydrophobic signal sequence of OspA. The primary translation product of the full length B. burgdorferl gene contains a hydrophobic N-terminal signal sequence which is a substrate for the attachment of a diacyl glycerol to the sulfhydryl side chain of the adjacent cysteine residue. Following this attachment, cleavage by signal peptidase II and the attachment of a third fatty acid to the N-terminus occurs. The complete lipid moiety is termed Pam$_3$Cys. It has been shown that lipidation of OspA is necessary for immunogenicity, since OspA lipoprotein with an N-terminal Pam$_3$Cys moiety stimulated a strong antibody response, while OspA lacking the attached lipid did not induce any detectable antibodies [Erdile et al., Infect. Immun., (1993), 61:81–90].

Published international patent application WO 91/09870 (Mikrogen Molekularbiologische Entwicklungs-GmbH) describes the DNA sequence of the ospC gene of B. burgdocferi strain Pko and the OspC (termed pC in this reference) protein encoded thereby of 22 kDa molecular weight. This sequence reveals that OspC is a lipoprotein that employs a signal sequence similar to that used for OspA. Based on the findings regarding OspA. one might expect that lipidation of recombinant OspC would be useful to enhance its immunogenicity; but, as discussed in above-referenced application Ser. No. 08/475,781, filed Jun. 7, 1995 (abandoned; the continuation of which is application Ser. No. 09/067,453, filed Apr. 28, 1998 (now U.S. Pat. No. 6,538, 118 B1)), the therein applicants experienced difficulties in obtaining detectable expression of recombinant OspC. It would be useful to enhance the immunogenicity of recombinant OspC. Moreover, it would be useful to have a multivalent Lyme Disease immunological composition which contains antigens against both North American and European Borrelia isolates.

Streptoccus pneumoniae causes more fatal infections world-wide than almost any other pathogen. In the U.S.A., deaths caused by S. pneumoniae rival in numbers those caused by AIDS. Most fatal pneumoccal infections in the U.S.A. occur in individuals over 65 years of age, in whom S. pneumoniae is the most common cause of community-acquired pneumonia. In the developed world, most pneumococcal deaths occur in the elderly, or in immunodeficient patents including those with sickle cell disease. In the less-developed areas of the world, pneumococcal infection is one of the largest causes of death among children less than 5 years of age. The increase in the frequency of multiple antibiotic resistance among pneumococci and the prohibitive cost of drug treatment in poor countries make the present prospect for control of pneumococcal disease problematical.

The reservoir of pneumococci that infect man is maintained primarily via nasopharyngeal human carriage. Humans acquire pneumococci first through aerosols or by direct contact. Pneumococci first colonize the upper airways and can remain in nasal mucosa for weeks or months. As many as 50% or more of young children and the elderly are colonized. In most cases, this colonization results in no apparent infection. In some individuals, however, the organism carried in the nasopharynx can give rise to symptomatic sinusitis of middle ear infection. If pneumococci are aspirated into the lung, especially with food particles or mucus, they can cause pneumonia. Infections at these sites generally shed some pneumococci into the blood where they can lead to sepsis, especially if they continue to be shed in large numbers from the original focus of infection. Pneumococci in the blood can reach the brain where they can cause meningitis. Although pneumococcal meningitis is less common than other infections caused by these bacteria, it is particularly devastating; some 10% of patients die and greater than 50% of the remainder have life-long neurological sequelae.

In elderly adults, the present 23-valent capsular polysaccharide vaccine is about 60% effective against invasive pneumococcal disease with strains of the capsular types included in the vaccine. The 23-valent vaccine is not effective in children less than 2 years of age because of their inability to make adequate responses to most polysaccharides. Improved vaccines that can protect children and adults against invasive infections with pneumococci would help reduce some of the most deleterious aspects of this disease.

The *S. pneumoniae* cell surface protein PspA has been demonstrated to be a virulence factor and a protective antigen. In published international patent application WO 92/14488, there are described the DNA sequences for the pspA gene from *S. pneumoniae* Rx1, the production of a truncated form of PspA by genetic engineering, and the demonstration that such truncated form of PspA confers protection in mice to challenge with live pneumococci.

In an effort to develop a vaccine or immunogenic composition based on PspA, PspA has been recombinantly expressed in *E. coli*. It has been found that in order to efficiently express PspA, it is useful to truncate the mature PspA molecule of the Rx1 strain from its normal length of 589 amino acids to that of 314 amino acids comprising amino acids 1 to 314. This region of the PspA molecule contains most, if not all, of the protective epitopes of PspA. However, immunogenicity and protection studies in mice have demonstrated that the truncated recombinant form of FspA is not immunogenic in naive mice. Thus, it would be useful to improve the immunogenicity of recombinant PspA and fragments thereof. Moreover, it would be highly desirable to employ a pneumococcal antigen in a combination or multivalent composition. For instance, influenza (Flu) is a problematical infection, especially in the elderly and the young, as well as pneumonia; and, yearly Flu shots are common, especially in North America. Thus, it would be desirable to be able to administer Flu and pneumococcal antigens in one preparation.

*Helicobacter pylori* is the spiral bacterium which selectively coloniizes human gastric mucin-secreting cells and is the causative agent in most cases of nonerosive gastritis in humans. Recent research activity indicates that *H. pylori*, which has a high urease activity, is responsible for most peptic ulcers as well as many gastric cancers. Many studies have suggested that urease, a complex of the products of the ureA and ureB genes, may be a protective antigen. However, until now it has not been known how to produce a sufficient mucosal immune response to urease without cholera toxin or related adjuvants.

Antigens or immunogenic fragments thereof stimulate an immune response when administered to a host. Such antigens, especially when recombinantly produced, may elicit a stronger response when administered in conjunction with adjuvant. Currently, alum is the only adjuvant licensed for human use, although hundreds of experimental adjuvants such as cholera toxin B are being tested. However, these adjuvants have deficiencies. For instance, while cholera toxin is a good adjuvant, it is highly toxic. On the other hand, cholera toxin B, while non-toxic, has no adjuvant activity. It would thus be desirable to provide immunological compositions capable of eliciting a strong response without the need for an adjuvant.

In certain instances when multiple antigens (two or more) are administered in the same preparation or sequentially, a phenomenon called efficacy interference occurs. Simply, due to the interaction of one or more antigens in the preparation with the host immunological system, the second or other antigens in the preparation fail to elicit a sufficient response, i.e., the efficacy of the latter antigen(s) is interfered with by the former antigen(s). It would thus be desirable to provide multivalent immunological compositions which do not give rise to this efficacy interference phenomenon; for instance, without wishing to necessarily be bound by any one particular theory, because the second antigen is a lipoprotein and as such is having an adjuvanting effect on the first antigen and, when in a combination composition with an adjuvant, a synergistic potentiating effect is obtained (whereby the first antigen is not interfering with the second antigen and vice versa).

More generally it would be desirable to enhance the immunogenicity of antigens by methods other than the use of an adjuvant, and to have the ability to employ such a means for enhanced immunogenicity with an adjuvant, so as to obtain an even greater immunological response.

Above-referenced application Ser No. 08/446,201 (now U.S. Pat No. 6,042,838 discloses that mucosal administration of killed whole pneurnococci, lysate of pneumococci or isolated and purified PapA, as well as immunogenic fragments thereof, particularly when administered with an adjuvant, provides protection in animals against pneumococcal colonization and systemic infection. It has now been surprisingly found that mucosal administration of other antigens, such as urease, along with a lipoprotein, elicits systemic and local responses in animals without the use of an adjuvant.

It is believed that heretofore the art has not taught or suggested: immunological compositions comprising at least one antigen and a lipoprotein, and, optionally, an adjuvant, more preferably an antigen, an antigenic lipoprotein and, optionally, an adjuvant, and methods for administering the same as a multivalent composition, or for administering those components simultaneously or sequentially, especially such compositions and methods having enhanced immunogenicity.

OBJECTS AND SUMMARY OF THE INVENTION

It is an object of the invention to provide immunological compositions and methods for making and using the same.

It is a further object of the invention to provide immunological compositions having enhanced immunogenicity; or, compositions the administration of which potentiates the immunological response.

It is another object of the invention to provide methods for inducing an immunological response, preferably a potentiated response, involving administration to a suitable host such immunological compositions.

It is yet an additional object of the invention to provide an immunological composition comprising at least one antigen and at least one lipoprotein and, optionally, an adjuvant, preferably such compositions wherein the lipoprotein is antigenic.

It is still a further object of the invention to provide a method for inducing or potentiating an immunological response comprising administering to a host, animal or human, at least one antigen and at least one lipoprotein, and optionally, an adjuvant; and more preferably such methods wherein the lipoprotein is antigenic.

It has surprisingly been found that administration to a host of at least one lipoprotein with at least one antigen provides an immunological response by the host. The imrounological response is generally better than that obtained by administration of the antigen alone.

Moreover, it has also surprisingly been found that administration to a host of at least one antigen, at least one lipoprotein and, optionally an adjuvant by either co-administration or by sequential administration (over a suitable time period such that each of the antigen, adjuvant and lipoprotein are present within the host at the same time) obtains an immunological response to the antigen by the host. This immunological response is generally better than that obtained by administration of the antigen alone or by administration of the antigen and adjuvant. Lipidated proteins appear to stimulate the immune response, in the manner of the adjuvant cholera toxin B.

Furthermore, it has additionally been surprisingly found that in these administrations the lipoprotein itself can be immunogenic or antigenic, e.g., be an antigen, and that not only is the immunological response to the antigen by the host obtained; but also, an immunological response to the antigenic lipoprotein is obtained. The immunological response to the antigenic lipoprotein can be as good as, or better than, that obtained by administration of the lipoprotein alone or with an adjuvant; and, the immunological response to the antigen can be better than that obtained by administering the antigen alone or the antigen and adjuvant.

The term lipoprotein as used herein is meant to exclude prior art lipopeptides; ergo, a lipoprotein can have more than 2 to 10 amino acids, or more than 18 to 20 amino acids, or greater than 24 amino acids, or 30 or more amino acids. Lipoproteins are larger molecules which reduce the amount of antigen and/or administrations of the antigen, despite a prejudice in the art against lipoproteins, e.g., Vaccine (1994) 12(14):1335, 1338 last line, column 1, to first line, column 2 ("soluble proteins . . . not immunogenic [by oral routes]"). Prior lipopeptides, due to their small size, can have at most one epitope whereas lipoproteins that can be used in the present invention can have more than one epitope, e.g. one B and one T, or can even be antigenic in their own right. Lipopeptides, in addition to being shorter and having less molecular weight than lipoproteins, and being difficult to synthesize because usually are made by Merrifield or other synthesis methods, differ from lipoproteins in that lipoproteins are larger, generally not made by Merrifield synthesis methods, and can be from isolation from natural sources or from recombinant techniques. That is, lipopeptides of the prior art were synthetically made, which limits their size to no more than about thirty amino acids. Lipoproteins are larger and of greater molecular weight than lipopeptides, and, unlike lipopeptides, are generally not made by Merrifield synthesis methods. Lipoproteins can be isolated from natural sources or produced by recombinant techniques. Further, lipoproteins are more soluble than lipopeptides. Additionally, peptides do not have quaternary or tertiary structure whereas proteins can have quaternary and/or tertiary structure. Based upon their ability to form tertiary structure, proteins have the ability to form functional domains which peptides cannot. Thus, there are several differences between prior "lipopeptides" and "lipoproteins" as used in this invention.

The lipoproteins formulations of the invention can be administered nasally and this is advantageous.

According to the present invention, it also has been found that a lipoprotein administered with an antigen according to the present invention is 500 times more potent then administration of a lipopeptide and an antigen.

Accordingly, the present invention provides an immunological composition comprising at least one antigen and at least one lipoprotein. The composition can further optionally, but not necessarily, comprise an adjuvant. Preferably the lipoprotein is an antigen. The immunological composition can be a vaccine.

The present invention further comprises a method for inducing an immunological response in a host comprising administering the aforementioned immunological composition. The method can be for inducing a protective response, e.g., when the immunological composition is a vaccine.

The present invention further comprises a method for inducing an immunological response comprising sequentially administering a first composition comprising an antigen, and a second composition comprising a lipoprotein. Optionally either the first or second composition, or both the first and second compositions can further comprise an adjuvant. Preferably the lipoprotein is an antigen. The sequential administration should be undertaken over a suitable period of time whereby each of the antigen, lipoprotein and optional adjuvant is present at the same time in the host; and, such a time period can be determined by the skilled artisan, from this disclosure, without undue experimentation and by methods within the ambit of the skilled artisan, such as host sera titrations involving analysis thereof for the presence of antigen or antibody by, for instance, ELISA analysis. The administration may be mucosal, e.g., intragastric or intranasal.

The present invention particularly involves methods for inducing an immunological response in a host comprising the steps of mucosally administering to the host at least one antigen, and mucosally administering to the host at least one lipoprotein. The administration can be simultaneous or sequential. The antigen may be a bacterial protein or fragment thereof, e.g. urease.

The "antigen" in the inventive compositions and methods can be any antigen to which one wishes to elicit an immunological response in a host, animal or human. For instance, without wishing to necessarily limit the invention, the antigen can be: a *Borrelia* antigen, e.g., OspA, OspC, OspB, OspD; a pneumococcal antigen, e.g., PspA; an influenza (Flu) antigen such as HA; a pertussis or whooping cough antigen such as the pertussis 69 KD polypeptide; a hepatitis antigen, e.g., hepatitis B antigen such as hepatitis B surface antigen; a *Helicobacter pylori* antigen such as urease; a rabies virus antigen, e.g., rabies G antigen; a flavivirus antigen, e.g., a Japanese encephalitis virus, Dengue virus or yellow fever virus antigen; a chicken pox virus antigen; a diphtheria antigen; a *C. tetani* antigen, e.g., tetanus toxoid; a mumps virus antigen; a measles virus antigen; a malaria antigen; a herpes virus antigen, such as an alphaherpesvirus, betaherpesvirus or gammaherpesvirus antigen, e.g., a herpes virus glycoprotein, for instance an equine herpesvirus antigen, e.g., gp13, gp14, gD, gp63, or gE, a pseudorabies virus antigen, e.g., gp50, gpII, gpIII, gpI, a herpessimplex virus antigen, e.g., gC, gD, a bovine herpes virus antigen, e.g., gI, a feline herpes virus antigen, e.g., gB, an Epstein-Barr virus antigen, e.g., gp220, gp340, or gH, or a human cytomegalovirus antigen, e.g., gB; a human immunodeficiency virus antigen, e.g., gp160 or gp120; a simian immunodeficiency virus antigen; a bovine viral diarrhea virus antigen; an equine influenza virus antigen; a feline leukemia virus antigen; a canine distemper virus antigen, e.g., HA or F glycoproteins; a canine adenovirus antigen, e.g., canine adenovirus type 2 antigen; a canine coronavirus antigen; a canine parainfluenza antigen; a canine parvovirus antigen; a Hantaan virus antigen; an avian influenza virus antigen e.g., a nucleoprotein antigen; a Newcastle Disease virus antigen, e.g., F, HN; an antigen of rous associated virus, e.g., an RAV-1 envelope antigen; an infectious bronchitis virus antigen, e.g., a matrix antigen or a preplomer antigen; an infectious bursal disease virus antigen; a cholera antigen; a tumor associated antigen; a feline immunodeficiency virus antigen; a foot-and-mouth disease virus antigen; a Marek's Disease Virus antigen; a *Staphylococci* antigen; a *Streptococci* antigen; a *Haemophilus influenza* antigen, e.g., group b polysaccharide-protein conjugates; a papilloma virus; a poliovirus antigen; a rubella virus antigen; a poxvirus, such as smallpox antigen, e.g., vaccinia; a typhus virus antigen; a typhoid virus antigen; a tuberculosis virus antigen; an HTLV antigen; or, other bacteria, virus or pathogen antigen, such as a bacterial or viral surface antigen or coat protein.

The antigen can be a known antigen; can be isolated from the bacteria, virus or pathogen; or, can be a recombinant antigen from expression of suitable nucleic acid coding therefor by a suitable vector, and isolation and/or purification of the recombinant antigen. The selection of the antigen is, of course, dependent upon the immunological response desired and the host.

The lipoprotein can be any lipoprotein which is compatible physiologically with the host. Most preferably it is a bacterial lipoprotein or a lipoprotein having a bacterial lipid moiety.

The lipoprotein is preferably itself also an antigen. Thus, the lipoprotein is preferably an outer membrane component of a pathogen, e.g., virus or bacteria, more preferably a lipoprotein which has an extrinsic or peripheral protein such that the lipoprotein is extracted with mild conditions or detergent without substantial denaturation or loss of lipid moiety (so as to retain epitopes). However, any antigenic lipoprotein can be employed in the practice of the invention. And, the lipoprotein can be isolated from a suitable physiological source, or from an organism, e.g., bacteria; or can be recombinantly produced. Thus, the lipidated *Borrelia* antigens, e.g., recombinant OspA, and, the lipidated OspA and *Borrelia* fractions containing lipidated proteins (isolated by mild conditions) disclosed in the applications referenced in the Reference to Related Applications, and in WO 90/04411 (incorporated herein by reference) can be used as the lipoprotein in the practice of the invention. Of course, the "antigen" and the "lipoprotein" in the invention are separate, different ingredients (such that, for instance, when the "lipoprotein" is OspA, it is not also the "antigen").

In application Ser. No. 08/475,781 filed Jun. 7, 1995 (abandoned; the continuation of which is application Ser. No. 09/067,453, filed Apr. 28, 1998 (now U.S. Pat No. 6,538,118 B1)) and incorporated herein by reference, recombinant lipoproteins, especially antigenic recombinant lipoproteins, for instance, those from expression of the leader sequence of OspA for the lipidation thereof, are disclosed; and, those recombinant lipoproteixis may be employed in the practice of the invention. As to expression of recombinant proteins, it is expected that the skilled artisan is familiar with the various vector systems available for such expression, e.g., bacteria such as *E. coli* and bacterial viruses, and the like.

The adjuvant can be any vehicle which would typically enhance the antigenicity of the antigen, e.g., a suspension or gel of minerals (for instance, alum, aluminum hydroxide or phosphate) on which the antigen is adsorbed; or a water-in-oil emulsion in which antigen solution is emulsified in mineral oil (e.g., Freund's incomplete adjuvant), sometimes with the inclusion of killed mycobacteria (e.g., Freund's complete adjuvant); or cholera toxin (sometimes with cholera toxin B, which may enhance the effect); or, any of the other adjuvants known in the art, or discussed in the Background of the Invention. The antigen and/or the lipoprotein can be absorbed onto or coupled with the adjuvant.

Presently preferred embodiments of the invention involve: alum as the adjuvant if an adjuvant is present; OspA, or a recombinant OspA leader/PspA, a recombinant OspA leader/OspC, a recombinant OspA leader/UreA of *H. pylori*, or, a recombinant OspA leader/UreB of *H. Pylori* as the lipoprotein (OspA leader/PspA is a recombinant lipoprotein having a lipidated moiety from expression of the OspA leader nucleic acid sequence and a protein moiety from expression of a pspA nucleic acid sequence; OspA leader/OspC is analogous to OspA leader/PspA, except that the protein moiety is from expression of an ospC nucleic acid sequence and OspA leader/ureA and OspA leader/ureB are also analogous to OspA leader/PspA, except that the protein moiety is from expression of a ureA or ureB nucleic acid sequence); and OspC or another *Borrelia* antigen, or an influenza antigen, e.g., HA (such as from influenza A, e.g., Texas strain), or urease as the antigen. Particular embodiments can include compositions: (i) comprising alum [adjuvant], OspA [lipoprotein] and another *Borrelia* antigen such as OspC [antigen]; (ii) comprising alum [adjuvant], OspA [antigen], and OspA leader/OspC [lipoprotein]; (iii) comprising alum [adjuvant], OspA leader/PspA [lipoprotein] and influenza antigen, e.g., influenza A HA [antigen] (iv) OspA [lipoprotein} and an *H. pylori* antigen, e.g., urease [antigen].

Other objects and embodiments of the invention are disclosed in or are obvious variants from the following description.

BRIEF DESCRIPTION OP THE DRAWINGS

In the following detailed description, reference is made to the accompanying drawings, wherein:

FIG. 1 is a graphical representation of the immune response of mice immunized with OspC formulations with or without purified lipidated OspA and with or without alum as an adjuvant as measured in an anti-OspC ELISA at day 63 after immunization; and FIG. 2 is a graphical representation of the immune response of mice immunized with OspC formulations with or without purified lipidated OspA and with or without alum as an adjuvant as measured in an anti-OspC ELISA at day 91 after immunization.

DETAILED DESCRIPTION OF THE INVENTION

Figure 1:
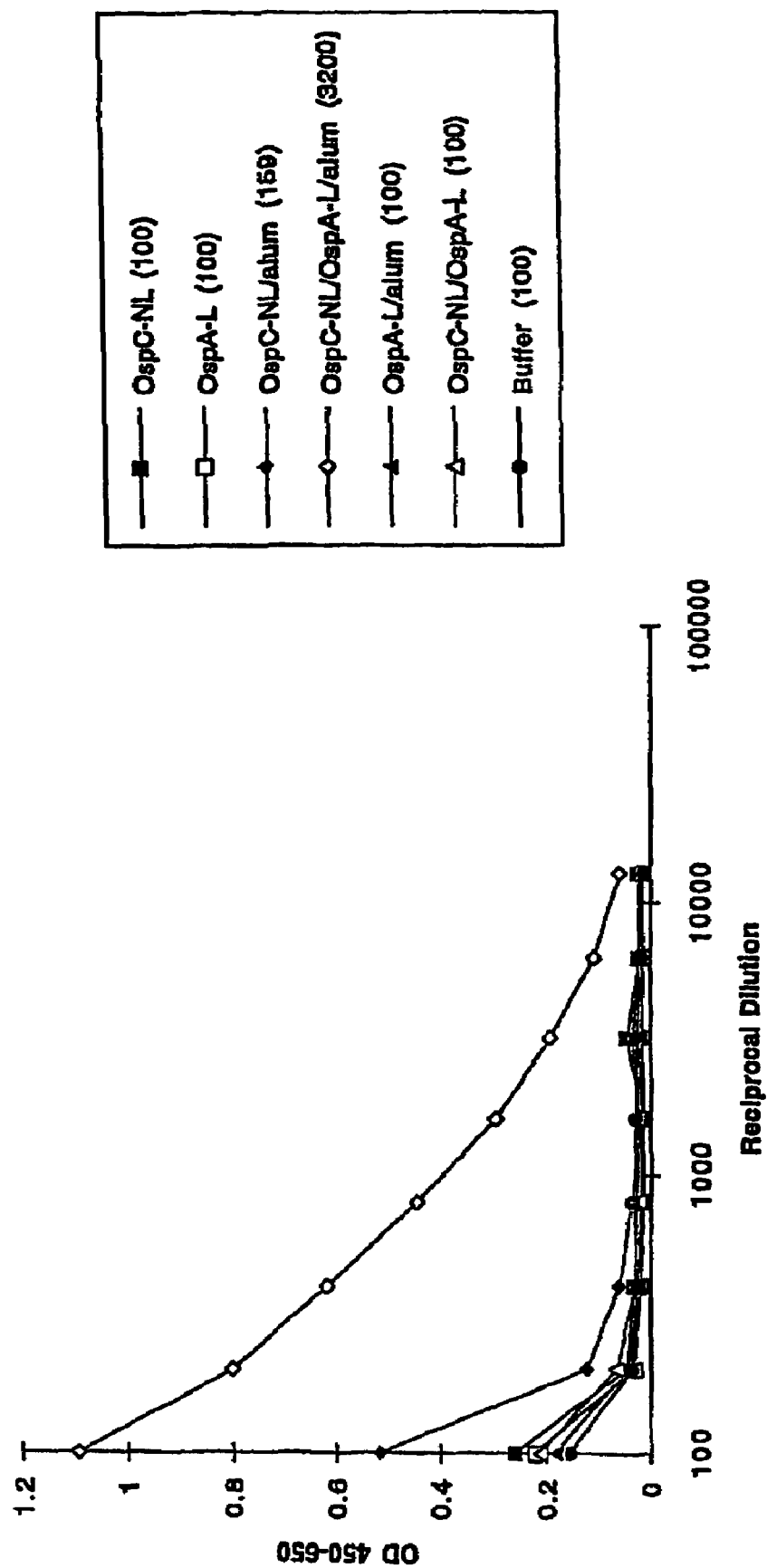

As discussed above, the invention involves immunological compositions and methods for making and using (e.g., administering) then which, in a broad sense, include immunological compositions comprising an antigen and a lipoprotein and optionally including an adjuvant; and the methods broadly include administering such compositions to a suitable host such that there is co-administration of the antigen and lipoprotein and optional adjuvant, or sequentially administering the components thereof.

It has now surprisingly been found that mucosal administration of an antigen, e.g., a bacterial protein or fragment thereof, and a lipoprotein produces both local and serum immune responses. The principal determinant of specific immunity at mucosal surfaces is secretory IgA (S-IgA) which is physiologically and functionally separate from the components of the circulatory immune system. S-IgA antibody responses may be induced locally by the application of suitable immunogens to a particular mucosal site. The bulk of mucosal S-IgA responses, however, are the results of immunity generated via the common mucosal immune system (CMIS) [Mestecky, J. *J. Clin Immunol.* (1987) 7:265–276], in which immunogens are taken up by specialized lympho-epithelial structures, collectively referred to as mucosa-associated lymphoid tissue (MALT). The best studied immunologic lympho-epithelial structures are the gut-associated lymphoid tissues (GALT), such as intestinal Peyer's patches. It is now clear, however, that other structurally and functionally similar lymphoid follicles occur at other mucosal surfaces, including those of the respiratory tract [Croituru, K., et al., in "Handbook of Mucosal Immunology" (Bienenstock, J., ed.) San Diego, Calif.: Academic Press, Inc. (1994), 141–149].

In the experimental results set forth in the Examples below, it is shown that mice can be effectively immunized by intranasal (i.n.) or intragastric (i.g.) installation of bacterial protein immunogens in conjunction with a lipoprotein such as OspA. Specific IgA- and IgG-secreting cells are induced in the salivary glands and stomachs (stomachs not shown) and specific IgA antibodies are induced in saliva (not shown). Strong circulatory immune responses are also induced with IgG and IgA antibodies in the serum. Accordingly, it appears that mucosal immunization with antigens along with lipoproteins is an effective route for stimulating common mucosal responses as well as circulatory antibody responses. Such immunization may be both therapeutic and prophylactic.

The determination of the amount of antigen, lipoprotein and optional adjuvant in the inventive compositions and the preparation of those compositions can be in accordance with standard techniques well known to those skilled in the pharmaceutical or veterinary arts. In particular, the amount of antigen, lipoprotein and adjuvant in the inventive compositions and the dosages administered are determined by techniques well known to those skilled in the medical or veterinary arts taking into consideration such factors as the particular antigen, the lipoprotein, the adjuvant, the age, sex, weight, species and condition of the particular patient, and the route of administration. For instance, dosages of particular antigens listed above for suitable hosts in which an immunelogical response is desired, are known to those skilled in the art, as is the amount of adjuvant typically administered therewith. Thus, the skilled artisan can readily determine the amount of antigen and optional adjuvant in compositions and to be administered in methods of the invention. Typically, an adjuvant is commonly used as 0.001 to 50 wt % solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt % (see, e.g., the Examples below).

The skilled artisan can refer to a known dosage for the particular antigen for a particular host to determine the amount of lipoprotein in compositions and administered in methods of the present invention, (if the lipoprotein is antigenic) such as the known dosages for OspA from the documents cited herein, or can scale the dosage for a particular host from the documents cited herein and the Examples below (e.g., with respect to OspA leader/PspA, OspA leader/Ospc, OspA leader/ureA, and OspA leader/ureB. Typically, however, the antigenic and/or recombinant lipoprotein is present in an amount on the order of micrograms to milligrams, or, about 0.001 to about 20 wt %, preferably about 0.01 to about 10 wt %, and most preferably about 0.05 to about 5 wt % (see, e.g., Examples below).

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA. Such determinations do not require undue experimentation from the knowledge of the skilled artisan, this disclosure and the documents cited herein. And, as discussed above, the time from for sequential administrations can be ascertained without undue experimentation.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut.

If nasal or respiratory (mucosal) administration is desired, compositions may be prepared as inhalables, sprays and the like and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions within the scope of this invention can contain a humectant to inhibit drying of the mucous membrane and to prevent irritation. Any of a variety of pharmaceutically acceptable humectants can be employed including, for example sorbitol, propylene glycol or glycerol. As with the thickeners, the concentration will vary with the selected agent, although the presence or absence of these agents, or their concentration, is not an essential feature of this invention.

Enhanced absorption across the mucosal and especially nasal membrane can be accomplished employing a pharmaceutically acceptable surfactant. Typically useful surfactants for compositions include polyoxyethylene derivatives of fatty acid partial esters of sorbitol anhydrides such as Tween 80, Polyoxynol 40 Stearate, Polyoxyethylene 50 Stearate and Octoxynol. The usual concentration is form 1% to 10% based on the total weight.

A pharmaceutically acceptable preservative can be employed to increase the shelf-life of the compositions. Benzyl alcohol may be suitable, although a variety of preservatives including, for example, Parabens, thimerosal, chlorobutanol, or benzalkonium chloride may also be employed. A suitable concentration of the preservative will be from 0.02% to 2% based on the total weight although there may be appreciable variation depending upon the agent selected.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form [e.g., whether the composition is to be formulated into a solution, a suspension, gel or another liquid form, or solid dosage form [e.g., whether the composition is to be formulated into a pill, tablet, capsule, caplet, time release form or liquid-filled form].

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lachrymal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the antigen, lipoprotein and optional adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below (e.g., from the Examples involving mice), and the knowledge of antigens and lipoproteins and adjuvants herein mentioned.

The present invention also includes a method for inducing an immunological response in a host wherein the antigen and lipoprotein are administered at one mucous membrane and a response is detectable at another mucous membrane, e.g. nasal administration and vaginal response. This aspect of the invention is particularly useful for the treatment or prevention of sexually transmitted diseases.

Suitable regimes for initial administration and booster doses or for sequential administrations also are variable, may include an initial administration followed by subsequent administrations; but nonetheless, may be ascertained by the skilled artisan, from this disclosure, the documents cited herein, the Examples below, and the knowledge of antigens, lipoproteins and adjuvants herein mentioned without undue experimentation.

The following Examples are provided for illustration and are not to be considered a limitation of the invention.

EXAMPLES

Example 1

Construction of a pET9a Expression Vector Containing a Hybrid ospA/pspA Gene

Specifically designed oligonucleotide primers were used in a PCR reaction to amplify the portion of the pspA gene of interest (in this case from amino acid 1 to 314) from the *S. pneumoniae* strain RX1.

The 5'-end primer had the nucleotide sequence: 5'-GGG ACA GCA TGC GAA GAA TCT CCC GTA GCC AGT-3' (PspNl) SEQ ID NO: 1).

The 3'-end primer had the nucleotide sequence: 5'-GAT GGA TCC TTT TGG TGC AGG AGC TGG TTT-3' (PspC370) (SEQ ID NO: 2).

The PCR reaction was as follows: 94° C. for 30 seconds to denature DNA; 42° C. for one minute for annealing DNA; and 72° C. for one minute for extension of DNA. This was carried out for 25 cycles, followed by a 5 minute extension at 72° C. This procedure introduced a stop codon at amino acid 315. The PCR product was purified using the Gene Clean II method (Bio101), and digested with SphI and BamHI.

The plasmid pLF100 was prepared as follows.

Plasmid pBluescript KS+ (Stratagene) was digested with XbaI and BamHI and ligated with a 900 bp XbaI-BamHI DNA fragment containing the complete coding region of *B. burgdorferi* strain ACA1 ospA gene, to form a lipoprotein fusion vector pLF100. This procedure is shown schematically in FIG. 1 of application Ser. No. 08/475,781, filed Jun. 7, 1995 (abandoned; the continuation of which is application Ser. No. 09/067,453, filed Apr. 28, 1998 (now U.S. Pat. No. 6,538,118 B1)) and incorporated herein by reference.

The vector pLF100 has been deposited with the American Type Culture Collection at Rockville, Md. on Feb. 2, 1995 under Accession No. 69750. This deposit was made under the terms of the Budapest Treaty.

pLF100 was digested with SphI and BamHI and the amplified pspA gene was ligated to this plasmid to form the plasmid pLF321, which contained the hybrid ospA-pspA gene. The hybrid gene was excised from pLF321 by digestion with NdeI and BamHI and cloned into the NdeI and BamHI sites of the plasmid vector pET9a to place the ospA-pspA hybrid gene under the control of a T7 promoter. The resulting plasmid is called pPA321-L. This process is shown schematically in FIG. 9 of application Ser. No. 08/475,781 filed Jun. 7, 1995 (abandoned; the continuation of which is application Ser. No. 09/067,453, filed Apr. 28, 1998 (now U.S. Pat. No. 6,538,118 B1)) and incorporated herein by reference.

Example 2

Construction of a pET9a Expression Vector Containing the pspA Gene

Specifically designed oligonucleotide primers were used a PCR reaction to amplify the portion of the pspA gene of interest (in this case from amino acid 1 to 314) from the *S. pneumoniae* strain RX1.

The 5'-end primer had the nucleotide sequence: 5'-GCT CCT GCA TAT GGA AGA ATC TCC CGT AGC C-3' (PspNL-2) (SEQ ID NO: 3)

The 3'-end primer had the nucleotide sequence: 5'-GAT GGA TCC TTT TGG TGC AGG AGC TGG TTT-3' (PspC370) (SEQ ID NO: 4).

The PCR reaction was as follows: 94° C. for 30 seconds to denature DNA; and 72° C. for one minute for annealing and extension of DNA. This was carried out for 25 cycles, which was followed by a 5 minute extension at 72° C. This procedure introduced a stop codon at amino acid 315. The PCR product was purified using the Gene Clean II method (Bio 101), and digested with NdeI and BamHI. The digested PCR product was cloned into the NdeI and BamHI sites of the plasmid vector pET9a to place the pspA gene under the control of a T7 promoter. The resulting plasmid is called pPA321-NL. This process is shown schematically in FIG. 10 of application Ser. No. 08/475,781, filed Jun. 7, 1995 (abandoned; the continuation of which is application Ser. No. 09/067,453, filed Apr. 28, 1998 (now U.S. Pat. No. 6,538,118 B1)) and incorporated herein by reference.

Example 3

Expression and Purification of Lipidated PspA

Plasmid pPA321-L was used to transform *E. coli* strain BL21(DE3)pLyS. The transformed *E. coli* was inoculated into LB media containing 30 μg/ml kanamycin sulfate and 25 μg/ml chloramphenicol. The culture was grown overnight in a flask shaker at 37° C.

The following morning 50 ml of overnight culture was transferred to 1 L LB media containing 30 μg/ml kanamycin sulfate and the culture was grown in a flask shaker at 37° C. to a level of OD 600 nm of 0.6–1.0, in approximately 3–5 hours. To the culture medium was added IPTG to a final concentration of 0.5 mM and the culture was grown for an additional two hours at 30° C. The cultures were harvested by centrifugation at 4° C. at 10,000×G and the cell pellet collected. Lipidated PspA was recovered from the cell pellet.

The cell pellet was resuspended in PBS at 30 g wet cell paste per liter PBS. The cell suspension was frozen and stored at −20° C. The cells were thawed to room temperature to effect lysis. DNase1 was added to the thawed material at a final concentration of 1 μg/ml and the mixture incubated for 30 minutes at room temperature, which resulted in a decrease in viscosity of the material.

The material was then chilled in an ice bath to below 10° C. and Triton™ X-114 was added as a 10% stock solution to a final concentration of 0.3 to 1%. The mixture was kept on ice for 20 minutes. The chilled mixture was then heated to 37° C. and held at that temperature for 10 minutes. This caused the solution to become very cloudy as phase separation occurred. The mixture was then centrifuged at about 20° C. for 10 minutes at 12,000×G, which caused a separation of the mixture into a lower detergent phase, an upper clear aqueous phase and a pellet. The lipidated PspA partitioned into the detergent phase. The detergent phase was separated from the other two phases, diluted 1:10 with a buffer comprising 50 mM Tris, 2 mM EDTA, 10 mM NaCl pH 7.5, and was stored at −20° C.

A Q-Sepharose column was prepared in a volume of 1 ml per 5 ml diluted detergent phase. The column was washed with 2 column volumes of a buffer comprising 50 mM Tris, 2 mM EDTA, 0.3% Triton™ X-100, 1M NaCl pH 4.0, and then equilibrated with 5 to 10 column volumes 50 mM Tris, 2 mM EDTA, 0.3% Triton™ X-100, 10 mM NaCl pH 4.0. The pH of the diluted detergent phase material was adjusted to 4.0, at which time a precipitation occurred. This material was passed through a 0.2 µM cellulose acetate filtering unit to remove the precipitated material. The filtered diluted detergent phase was applied to the Q-Sepharose column and the flow through (containing PA321-L) was collected. The column was washed with 1–2 column volumes of 50 mM Tris, 2 mM EDTA, 0.3% Triton™ X-100, 10 mM NaCl pH 4.0, and the flow through was pooled with the previous flow through fraction. The pH of the flow through pool was adjusted to 7.5. The bound material, contaminating E. coli proteins, was eluted from the Q-Sepharose with 2 column volumes of 50 mM Tris, 2 mM EDTA, 0.3% Triton™ X-100, 1M NaCl pH 4.0. A schematic of the purification process described in this Example is shown in FIG. 11 of application Ser. No. 08/475,781, filed Jun. 7, 1995 (abandoned; the continuation of which is application Ser. No. 09/067,453, filed Apr. 28, 1998 (now U.S. Pat. No. 6,538,118 B1)) and incorporated herein by reference.

Example 4

Expression and Purification of Non-lipidated PspA

Plasmid pPA321-NL was used to transform E. coli strain BL21(DE3)pLyS. The transformed E. coli was inoculated into LB media containing 30 µg/ml kanamycin sulfate and 25 µg/ml chloramphenicol. The culture was grown overnight in a flask shaker at 37° C.

The following morning 50 ml of overnight culture was transferred to 1 L LB media containing 30 µg/ml kanamycin sulfate and the culture was grown in a flask shaker at 37° C. to a level of OD 600 nm of 0.6–1.0, in approximately 3–5 hours. To the culture medium was added IPTG to a final concentration of 0.5 mM and the culture was grown for an additional two hours at 30° C. The cultures were harvested by centrifugation at 4° C. at 10,000×G and the cell pellet collected. Non-lipidated PspA was recovered from the cell pellet.

The cell pellet was resuspended in PBS at 30 g wet cell paste per liter PBS. The cell suspension was frozen and stored at −20° C. The cells were thawed to room temperature to effect lysis. DNaseI was added to the thawed material at a final concentration of 1 µg/ml and the mixture incubated for 30 minutes at room temperature, which resulted in a decrease in viscosity of the material. The mixture was centrifuged at 4° C. at 10,000×G, and the cell supernatant saved, which contained non-lipidated PspA. The pellet was washed with PBS, centrifuged at 4° C. at 10,000×G and the cell supernatant pooled with the previous cell supernatant.

A MonoQ column (Pharmacia) was prepared in a volume of 1 ml per 2 ml cell supernatant. The column was washed with 2 column volumes of a buffer comprising 50 mM Tris, 2 mM EDTA, 1M NaCl pH 7.5, and then equilibrated with 5 to 10 column volumes of a buffer comprising 50 mM Tris, 2 mM EDTA, 10 mM NaCl pH 7.5. The cell supernatant pool was applied to the Q-Sepharose column and the flow through was collected. The column was washed with 2–5 column volumes of 50 mM Tris, 2 mM EDTA, 10 mM NaCl pH 7.5, and the flow through pooled with the previous flow through.

The elution of bound proteins began with the first step of a 5–10 column volume wash with 50 mM Tris, 2 mM EDTA, 100 mM NaCl pH 7.5. The second elution step was a 5–10 column volume wash with 50 mM Trie, 2 mM EDTA, 200 mM NaCl pH 7.5. The non-lipidated PspA was contained in this fraction. The remaining bound contaminating proteins were removed with 50 mM Tris and 2 mM EDTA pH 7.5 with 300 mM-1M NaCl.

A schematic of the purification process described in this Example is shown in FIG. 12 of application Ser. No. 08/475,781, filed Jun. 7, 1995 (abandoned; the continuation of which is application Ser. No. 09/061,453, filed Apr. 28 1998 (now U.S. Pat. No. 6,538,118 B1)) and incorporated herein by reference.

Example 5

Immunogenicity of Recombinant Lipidated PspA

Purified recombinant lipidated PspA, prepared as described in Example 3, was tested for immunogenicity in mice and compared to that from non-lipidated PspA prepared as described in Example 4. For this study, CBA/N mice were immunized subcutaneously in the back of the neck with 0.5 ml of the following formulations at the indicated PspA antigen concentrations.

| Formulation | PspA Antigen Concentration |
| --- | --- |
| Native PspA molecule of the RX1 strain (Native RX1) | 200 ng/ml |
| Non-Lipidated Recombinant PspA (pPA-321-NL) Alone in PBS* | 200 and 1000 ng/ml |
| Non-Lipidated Recombinant PspA (pPA-321-NL) Adsorbed to Alum | 200 and 1000 ng/ml |
| Lipidated Recombinant PspA (pPA-321-L) Alone in PBS | 200 and 1000 ng/ml |
| Lipidated Recombinant PspA (pPA0321-NL) Adsorbed to Alum* | 200 and 1000 ng/ml |
| Alum* | 0 ng/ml |
| PBS | 0 ng/ml |

*Alum was Hydrogel at a concentration of 200 µg/ml

Four mice were immunized on days 0 and 21 for each dosage of the formulations. The mice were then bled on day 35 and subsequently challenged with S. pneumoniae of A66 strain. The days of survival after challenge for the mice were recorded and surviving mice were bled on days 36, 37, 42 and 46. From these subsequent bleeds the blood was assayed for the number of colony forming units (CFU) of S. pneumoniae/ml. The sera taken on day 35 were assayed by ELISA for antibodies against PspA using ELISA. The days to death for the challenged mice are shown in the following table.

Survival in Immune and Non-Immune CBA/M Mice

| | Immunization | | | Efficacy | | | |
|---|---|---|---|---|---|---|---|
| Group | Antigen | dose in μg | Alum | Days to Death | $p$ value time to death* | Alive: Dead | $p$ value Survival* |
| #1A | pPA-321-L | 1.0 | − | 4x > 14 | 0.01 | 4:0 | 0.01 |
| #1B | PpA-321-L | 0.2 | − | 4x > 14 | 0.01 | 4:0 | 0.01 |
| #2A | pPA-321-L | 1.0 | + | 4x > 14 | 0.01 | 4:0 | 0.01 |
| #2B | pPA-321-L | 0.2 | + | 4x > 14 | 0.01 | 4:0 | 0.01 |
| #3A | pPA-321-NL | 1.0 | − | 1, 1, 2, 2 | n.s. | 0:4 | n.s. |
| #3B | pPA-321-NL | 0.2 | − | 1, 1, 2, ≧ 15 | n.s. | 1:3 | n.s. |
| #4A | pPA-321-NL | 1.0 | + | 4x > 14 | 0.01 | 4:0 | 0.01 |
| #4B | pPA-321-NL | 0.2 | − | 4x > 14 | 0.01 | 4:0 | 0.01 |
| #5 | FL-Rx1 | 0.2 | − | 4x > H | 0.01 | 4:0 | 0.01 |
| #6 | none | 0.0 | + | 1, 1, 3, 6 | n.s. | 0:4 | n.s. |
| #7 | none | 0.0 | − | 1, 1, 1, ≧ 15 | n.s. | 1:3 | n.s. |
| | pooled none | 0.0 | | 5x1, 3, 6, ≧ 15 | — | 1:7 | |

Note:
*indicates versus pooled controls; time to death, by one tailed two sample rank test; survival, by one tailed Fisher Exact test. Calculations have been done using "one tail" since we have never observed anti-PspA immunity to consistently cause susceptibility.

The number of CFU in the blood of the nice are shown in the table below.

Bacteremia in Immune and Non-Immune CBA/M Mice

| | Immunization | | | $Cog_{10}$ CFU | | | |
|---|---|---|---|---|---|---|---|
| Group | Antigen | dose in μg | Alum | 1 day | 2 day | 6 day | 7 day |
| #1A | pPA-321-L | 1.0 | − | ≦1.6, 1.9, 2.1, 2.5 | 4x ≦ 1.6 | 4x ≦ 1.6 | n.d. |
| #1B | pPA-321-L | 0.2 | − | 3x ≦ 1.6, 1.7 | 4x ≦ 1.6 | 4x ≦ 1.6 | n.d. |
| #2A | pPA-321-L | 1.0 | + | 2x ≦ 1.6, 1.7, 2.9 | 3x ≦ 1.6, 1.7 | 4x ≦ 1.6 | n.d. |
| #2B | pPA-321-L | 0.2 | + | 2x ≦ 1.6, 1.7, 1.7 | 4x ≦ 1.6 | 4x ≦ 1.6 | n.d. |
| #3A | pPA-321-NL | 1.0 | − | ≦1.6, 1.7, d, d | d, d, d, d | d, d, d, d | d, d, d, d |
| #3B | pPA-321-NL | 0.2 | − | 2x > 7, d, d | ≦1.6, d, d, d | ≦1.6, d, d, d | n.d., d, d, d |
| #4A | pPA-321-NL | 1.0 | + | 2x ≦ 1.6, 6.7, >7 | 3x ≦ 1.6, 1.7 | 4x ≦ 1.6 | n.d. |
| #4B | pPA-321-NL | 0.2 | + | ≦1.6, 1.7, 2.1, 2.4 | 4x ≦ 1.6 | 4x ≦ 1.6 | n.d. |
| #5 | FL-Rx1 | 0.2 | − | 2x ≦ 1.6, 2.6, 2.7 | 4x ≦ 1.6 | 4x ≦ 1.6 | n.d. |
| #6 | none | 0.0 | + | ≦1.6, 4.1, >7, d | ≦1.6, 5.1, d, d | 6.1, d, d, d | d, d, d, d |
| #7 | none | 0.0 | − | 1.7, >7, >7, d | ≦I.6, d, d, d | ≦1.6, d, d, d | n.d, d, d, d |
| | pooled none | 0.0 | | ≦1.6, 4.1, >7, >7, d | 2x ≦ 1.6, 5.1, d, d, d, d, d | ≦1.6, 6.1 d, d, d, d, d | n.d, d, d, d, d, d |

Note:
1 colony at the highest concentration of blood calculated out to 47 CFU or Log 1.7. Thus "1.6" indicates no colonies counted. >10$^7$ indicates that the mouse was alive but the number of colonies at the highest dilution was too high to count, "d" indicates the nice had died prior to assay.

These results indicate that the recombinant protein was not protective when injected alone. The recombinant antigen adjuvanted with alum and/or PAM$_3$cys lipidation was immunogenic and protective. The native full length PspA antigen did not need an adjuvant to be protective. The CFU results indicate that mice protected by immunization cleared the challenging S. pneumoniae from the blood in two days.

ELISA analysis of sera taken on day 35 indicated that there was a good correlation between protection of the mice from S. pneumoniae challenge and the induction of measurable antibody responses. No detectable antibody responses were observed in the sera of mice immunized with the non-lipidated antigen (pPA-321-NL) in saline or to the negative controls that did not contain PspA antigen, (as shown in the table below). Good antibody responses were detected to the Native RX1 PspA antigen and to the recombinant PspA when it was lipidated with PAM$_3$cys and/or adsorbed to alum.

ELISA Analysis of Day 35 Mouse Sera

| PspA Antigen | Alum Adsorption | PspA Dose (μg/mouse) | Resulting OD at Indicated Dilution of the Antisera* | | | | | |
|---|---|---|---|---|---|---|---|---|
| | | | 600 | 1200 | 2400 | 4800 | 9600 | 19200 |
| pPA-321-L | No | 0.1 | 0.885 (0.082) | 0.497 (0.043) | 0.271 (0.025) | 0.146 (0.017) | 0.075 (0.012) | 0.039 (0.009) |
| pPA-321-L | No | 0.5 | 1.857 (0.060) | 1.437 (0.137) | 1.108 (0.150) | 0.750 (0.139) | 0.459 (0.092) | 0.284 (0.057) |
| pPA-321-L | Yes | 0.1 | 1.373 (0.325) | 1.048 (0.376) | 0.745 (0.362) | 0.490 (0.304) | 0.288 (0.197) | 0.171 (0.147) |
| pPA-321-L | Yes | 0.5 | 1.202 (0.162) | 0.787 (0.184) | 0.472 (0.187) | 0.296 (0.102) | 0.162 (0.061) | 0.087 (0.035) |
| pPA-321-NL | No | 0.1 | 0.022 (0.035) | 0.030 (0.060) | 0.014 (0.024) | 0.007 (0.018) | 0.006 (0.005) | 0.001 (6.001) |
| pPA-321-NL | No | 0.5 | 0.029 (0.035) | 0.014 (0.014) | 0.008 (0.007) | 0.003 (0.004) | 0.002 (0.002) | 0.002 (0.002) |
| pPA-321-NL | Yes | 0.1 | 0.822 (0.181) | 0.481 (0.166) | 0.278 (0.085) | 0.154 (0.051) | 0.082 (0.029) | 0.042 (0.015) |
| pPA-321-NL | Yes | 0.5 | 1.017 (0.139) | 0.709 (0.128) | 0.447 (0.101) | 0.253 (0.057) | 0.141 (0.034) | 0.075 (0.020) |
| Native RX1 | No | 0.1 | 1.367 (0.084) | 1.207 (0.060) | 0.922 (0.070) | 0.608 (0.077) | 0.375 (0.048) | 0.209 (0.029) |
| None | NO | 0 | 0.018 (0.003) | 0.012 (0.008) | 0.009 (0.003) | 0.005 (0.002) | 0.005 (0.002) | 0.005 (0.002) |
| None | Yes | 0 | 0.013 (0.006) | 0.009 (0.008) | 0.004 (0.004) | 0.004 (0.003) | 0.001 (0.001) | 0.000 (0.000) |

*The OD is the mean of the result of the four tested animals and the standard deviation is in parentheses.

To determine whether protection was at least in part mediated by the anti-PspA antibody responses, a passive experiment was run. BALB/c mice were immunized with 0.5 μg of recombinant lipidated PspA alone or absorbed to alum, or with recombinant non-lipidated PspA adsorbed to alum on days 0 and 21; and were bled on day 35. The anti-sera were diluted 1:3 or 1:15 in saline and 0.1 ml of the dilution was injected i.p. into two mice for each dilution. A ⅓ dilution of normal BALB/c mouse serum was used as a negative control. Subsequently one hour after passive immunization, the animals were challenged i.v. with the WU2 strain of *S. pneumoniae* (15,000 CFU). Mice passively immunized with anti-PspA sera were protected as compared to those mice that received dilutions of normal mouse sera as shown in the following table.

Passive Protection of BALB/c to WU2

| Immunizing Formulation PepA Antigen | Alum | PepA Dose (μg/animal) | Dilution of Serum | Days to Daath Poet Challenge |
|---|---|---|---|---|
| pAP-321-L | No | 0.5 | 3 | 4, >7 |
| | | | 15 | 2, 4 |
| pPA-321-L | Yes | 0.5 | 3 | >7, >7 |
| | | | 15 | 4, >7 |
| pPA-321-NL | Yes | 0.5 | 3 | 2, 4 |
| | | | 15 | >7, >7 |
| None | No | 0 | 3 | 2,2 |

Example 6

Combination PepA/Plu Vaccine

Purified recombinant lipidated PspA, prepared as described in Example 3, and non-lipidated PspA prepared as described in Example 4 were combined with split flu antigen from the A/Texas strain.

These combinations and the flu antigen alone were formulated either in saline or adsorbed to alum in saline. The alum when added was kept constant at 100 μg/injection and the PspA was kept constant at 0.5 μg/injection. The flu antigen was diluted to concentrations of 0.5, 0.1, 0.02 and 0.004 μg/injection. Four BALB/c mice for each of the formulations were immunized on days 0 and 21, and were then bled on day 35. The sera from the immunized mice were then assayed for their ability to inhibit the agglutination or chicken red blood cells by A/Texas HA antigen. The resulting hemagglutination inhibition (HAI) titers are shown in the following table.

| Flu Antigen | PspA Antigen | Alum Adsorption | Flu HA Dose (μg/injection) | GMT of HAI Titer | STD of GMT of RAT Titer |
|---|---|---|---|---|---|
| A/Texas | — | + | 0.5 | 28.1 | 3 |
| A/Texas | — | + | 0.1 | 21.8 | 6.6 |

-continued

| Flu Antigen | PspA Antigen | Alum Adsorption | Flu HA Dose (µg/injection) | GMT of HAI Titer | STD of GMT of RAT Titer |
|---|---|---|---|---|---|
| A/Texas | — | + | 0.02 | 22.8 | 52 |
| A/Texas | — | + | 0.004 | 16.1 | 3.8 |
| A/Texas | — | − | 0.5 | 12.4 | 5.3 |
| A/Texas | — | − | 0.1 | 23.8 | 3.3 |
| A/Texas | — | − | 0.02 | 19.2 | 2.8 |
| A/Texas | — | − | 0.004 | 11.9 | 3.7 |
| A/Texas | pPA-321-L | + | 0.5 | 794.8 | 2.6 |
| A/Texas | pPA-321-L | + | 0.1 | 452.5 | 2.7 |
| A/Texas | pPA-321-L | + | 0.02 | 54.2 | 6.9 |
| A/Texas | pPA-321-L | + | 0.004 | 36.7 | 4.9 |
| A/Texas | pPA-321-L | − | 0.5 | 51.9 | 4 |
| A/Texas | pPA-321-L | − | 0.1 | 27.1 | 5.1 |
| A/Texas | pPA-321-L | − | 0.02 | 19.2 | 3.3 |
| A/Texas | pPA-321-L | − | 0.004 | 15.4 | 3.4 |
| A/Texas | pPA-321-NL | + | 0.5 | 174.5 | 2.7 |
| A/Texas | pPA-321-NL | + | 0.1 | 59.1 | 3.4 |
| A/Texas | pPA-321-NL | + | 0.02 | 19.2 | 5.1 |
| A/Texas | pPA-321-NL | + | 0.004 | 14.8 | 3.1 |
| A/Texas | pPA-321-NL | − | 0.5 | 35.1 | 2.7 |
| A/Texas | pPA-321-NL | − | 0.1 | 23.8 | 3 |
| A/Texas | pPA-321-NL | − | 0.02 | 14.8 | 2.9 |
| A/Texas | pPA-321-NL | − | 0.004 | 10.2 | 2.6 |
| None | None | − | 0 | 7.1 | 1.9 |

Example 7

Expression and Purification of Non-Lipidated OspC.

*E. coli* JM 109 transformants containing plasmid vector containing chromosomal gene fragment encoding non-lipidated OspC were prepared and grown as described in WO 91/09870. The cultures were harvested, the culture medium centrifuged at 10,000×G for 10 minutes at 4° C., the supernatant discarded and the pellet collected.

The cell pellet was first resuspended in lysis buffer A, namely 50 mM Tris-HCl pH 8.0, 2 mM EDTA, 0.1 mM DTT, 5% glycerol and 0.4 mg/ml lysozyme, and the suspension stirred for 20 minutes at room temperature. TRITON™ X-100 then was added to the cell suspension to a concentration of 1 wt %, DNase I was added to a concentration of 1 µg/ml, and the suspension stirred at room temperature for a further 20 minutes to effect cell lysis. Sodium chloride next was added to the cell suspension to a concentration of 1M and the suspension again stirred at 4° C. for a further 20 minutes. The suspension then was centrifuged at 20,000×G for 30 minutes, the resultant supernatant separated from the pellet and the pellet was discarded.

The separated supernatant was dialyzed against a buffer comprising 50 mM Tris pH 8, 2 mM EDTA. The supernatant next was loaded onto a DEAE-Sepharose CL-6B column and the non-lipidated OspC was collected in the column flow-through. The flow-through was dialyzed against a 0.1 M phosphate buffer, pH 6.0.

The dialyzed flow-through next was bound to a S-Sepharose fast flow column equilibrated with 0.1M phosphate buffer, pH 6.0. Purified non-lipidated OspC then was eluted from the S-Sepharose column using the dialysis buffer with 0.15 M NaCl added.

The aqueous solution of highly purified non-lipidated OspC was analyzed by Coomassie stained gels. The purity of the product was estimated to be greater than 80%.

Example 8

Potentiation of Response to Non-lipidated OspC with Lipidated OspA

Purified recombinant non-lipidated OspC, prepared as described in Example 7, was tested for immunogenicity in mice in combination with or without purified lipidated OspA (prepared as described in WO 92/14488). Formulations were administered with or without alum as an adjuvant. The antigen dose tested in this experiment was 1 µg per dose. For this study, 4 to 8 week old female C3H/He mice were immunized on day 0 and boosted on days 21 and 42.

Three representative animals were exsanguinated on days 21, 42, 63 and 91. ELISA testing was performed on these sera using purified non-lipidated OspC as the coating antigen.

Figure 2:
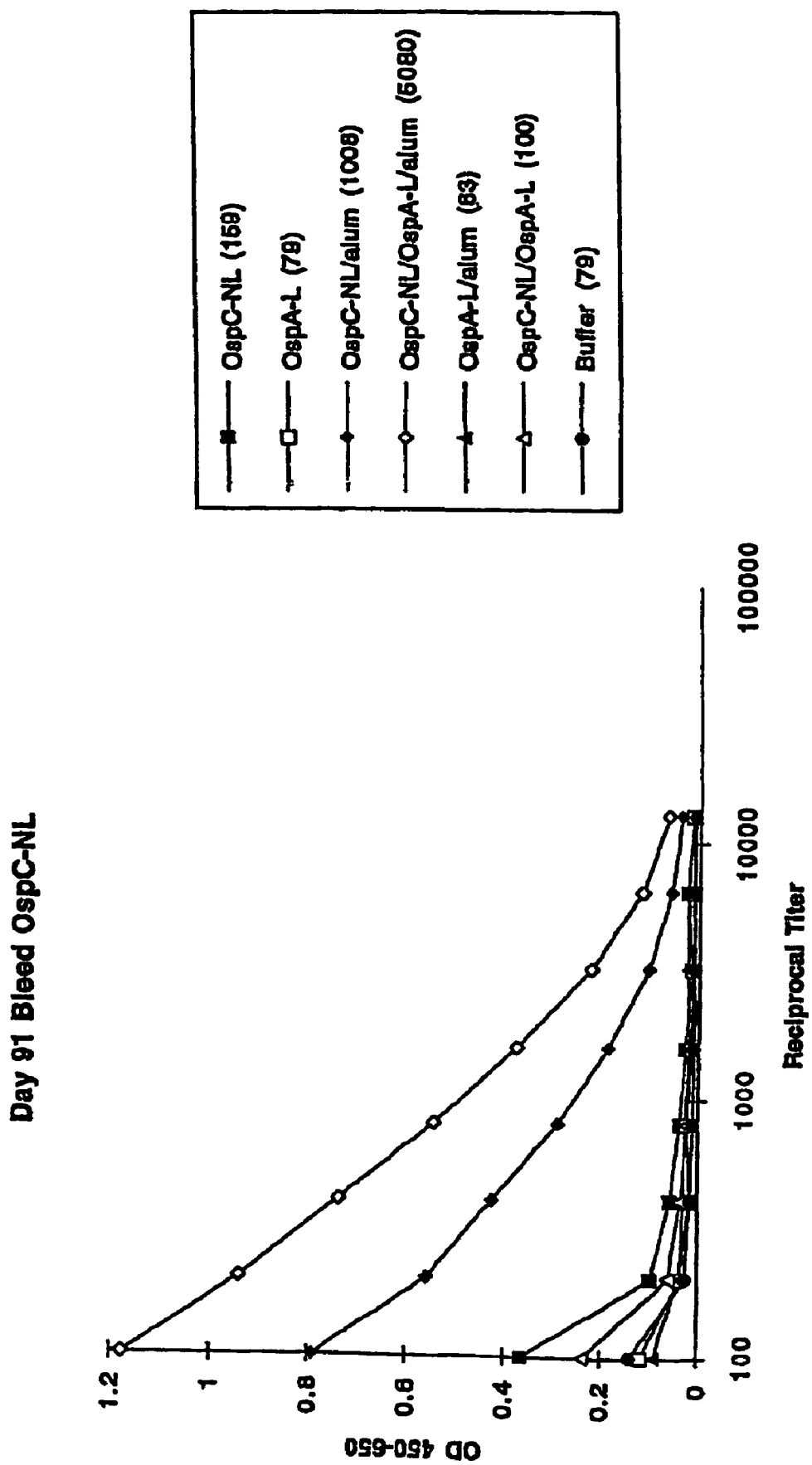

The only detectable OspC ELISA responses generated in this study were with the formulation of OspC on alum. However, when lipidated OspA was included on the alum the OspC ELISA response was 20-fold higher on day 63 (as shown in FIG. 1) and 5-fold higher on day 91 (as shown in FIG. 2). When lipidated OspA was included in the formulation without alum there was no apparent effect on the immune response.

Example 9

Salivary Gland ELISPOT Analysis of Response to Urease with OspA

Mice (CH3/HeN; 4–5/group) were immunized by mucosal routes with the antigens indicated in the table below, on days 0 and 28. Proteins were diluted in PBS to a final volume of 25 µl for intranasal and 0.5 ml for intragastric. The mice were sacrificed for ELISPOTS at 15–17 days after the second immunization.

The ELISPOT protocol was derived from the one described by Mega et al., *J. Immunol.* (1992), 148:2030–2039. The salivary glands were taken just after sacrifice of the mouse, and placed immediately in a large volume of RPMI 1640 medium (Gibco). The organs were cut in small pieces (1×1 mm) using an automated tissue chopper (Mc Illwain tissue chopper, The Mickle Laboratory Engineering, Gilford, U.K.), and then digested in 2 ml of RPMI 1640 medium containing 5% FCS and 1 mg/ml of collagenase type IV (Sigma) for 30 minutes at 37° C. with gentle agitation. The digested cells and fragments were passed through a 70 μM filter (Falcon), and the digestion was repeated three more times. The digested cells were pooled and washed twice in a large volume of medium. The pooled cells were then lysed using Gey's solution for 4 minutes on ice. After two more washes, the cells were resuspended in 2 ml of medium (+5% FCS), counted and aliquoted in 96 well nitrocellulose plates (MILLIPORE). The plates had been coated overnight with 20 μg/ml of jackbean urease (Boehringer Mannheim) or 10 μg/ml OspA (Connaught) in PBS at 4° C., and then saturated with complete medium for 1 hour at 37° C. Two five-fold dilutions of the cells were loaded in the wells (100 μl/well) in quadruplicate for each dilution and each isotype. After 4–16 hours at 37° under 5% CO2, the cells were lysed 2×5 minutes in PBS/Tween 20 (0.005%) and biotinylated anti-isotypes antibodies (Amersham) added for two hours at room temperature (dilution 1/1000). After 3 washes with PBS Tween, biotinylated streptavidin peroxydase complex (Amersham) was added for 1 hour (dilution 1/500), and then spots revealed with 3,9-aminoethylcarbazole (SIGMA). Once the plates dried, the spots were numerated under a dissecting microscope (magnification 16 or 40×). The values represent the means for 4 wells averaged for each group of animals.

As shown in the table below, it was found that lipidated OspA lipoprotein administered by mucosal routes without any added adjuvant induced very strong local IgG and IgA responses, while non-lipidated OspA did not induce any detectable responses. It was also found that OspA had a powerful adjuvant effect on the local response to urease.

| μg Jackbean Ure | OspA | Route | Anti Ure Spots/10⁶ Cells | | Anti Osp Spots/10⁶ Cells | |
|---|---|---|---|---|---|---|
| | | | IgA | IgG | IgA | IgG |
| — | 1 L | i.n. | n.d. | n.d. | 583 | 345 |
| — | 1 NL | i.n. | n.d. | n.d. | 4 | 2 |
| 20 | — | i.n. | 11 | 0 | n.d. | n.d. |
| 20 | 1 L | i.n. | 189 | 18 | 742 | 257 |
| 20 | 10 L | i.n. | 191 | 39 | 1237 | 174 |
| 20 + CT 10 μg | — | i.n. | 478 | 42 | n.d. | n.d. |
| 20 | — | i.n., i.g. | 0 | 1 | 25 | 0 |
| 20 | 10 L | i.n., i.g. | 322 | 31 | 1919 | 177 | i.n. = intransal
i.n., i.g. = intransal & intragastric (the indicated dose was given by each route)
L = lipidated OspA; NL = non-lipidated OspA
CT = cholera toxin (10 μg CTB + 10 ng CTX/mouse (PMSV))
n.d. = not determined Example 10

ELISA Assay to Measure Serum Antibodies Against OspA and Urease

Mice (CH3/HeN; 4–5/group) were immunized by mucosal routes with the antigens indicated in the table in Example 9 on days 0 and 28. Proteins were diluted in PBS to a final volume of 25 μl for intranasal and 0.5 ml for intragastric. Blood was taken 9 days after the second immunization.

For the ELISA assay, flat-bottomed 96 well microliter plates (Dynatech) were coated with 100 μl/well of 1 μg/ml OspA (Connaught) or 2 μg/ml jackbean urease (Boehringer Mannheim), diluted in 0.1 M sodium carbonate buffer, pH 9.6. Plates were coated overnight at room temperature.

Figure 3:
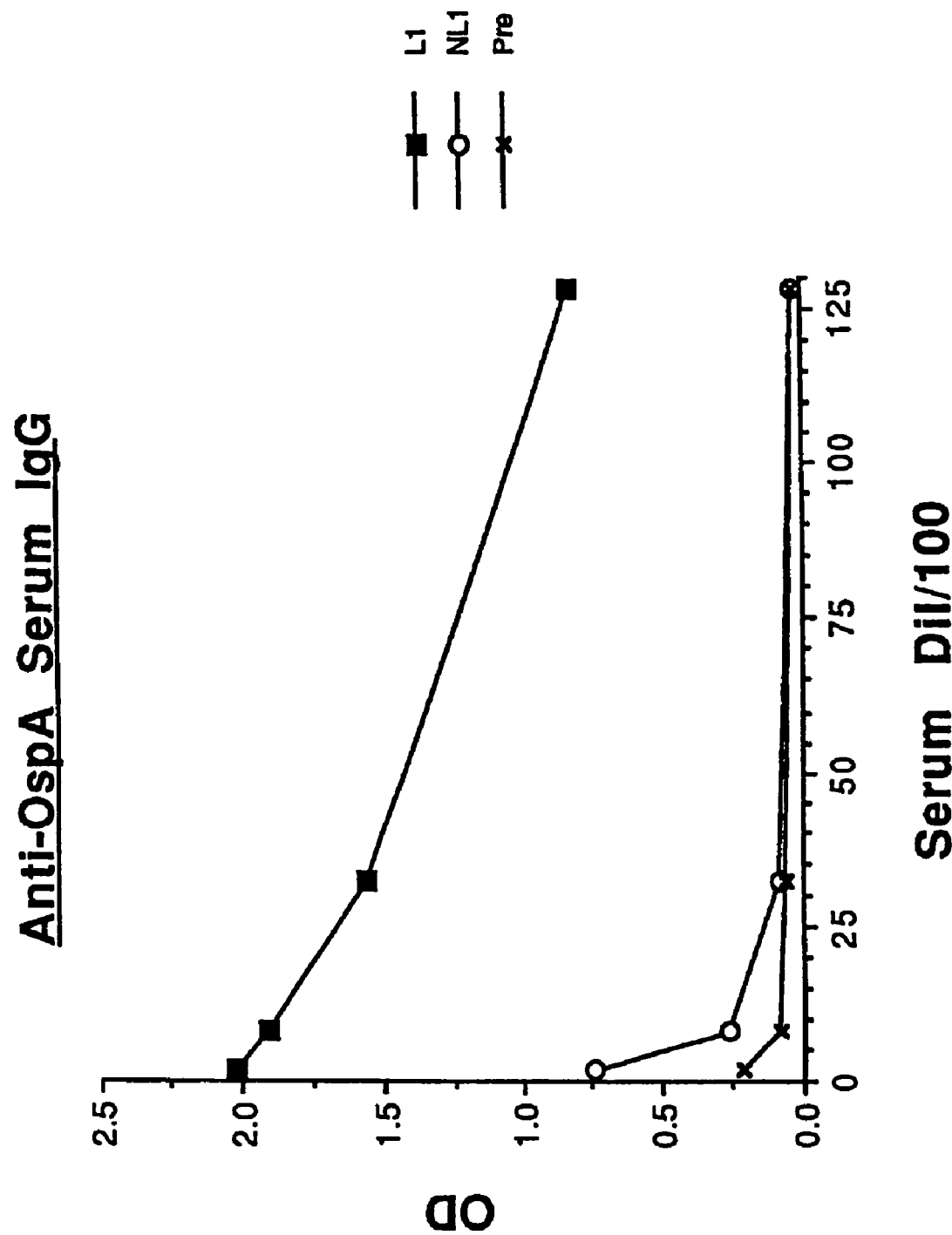
FIG. 3 is a graphical representation of the immune response of mice immunizing twice, intranasally, with either lipidated or non-lipidated OspA as measured in an anti-OspA ELISA at day 9 after the second immunization.
Figure 4:
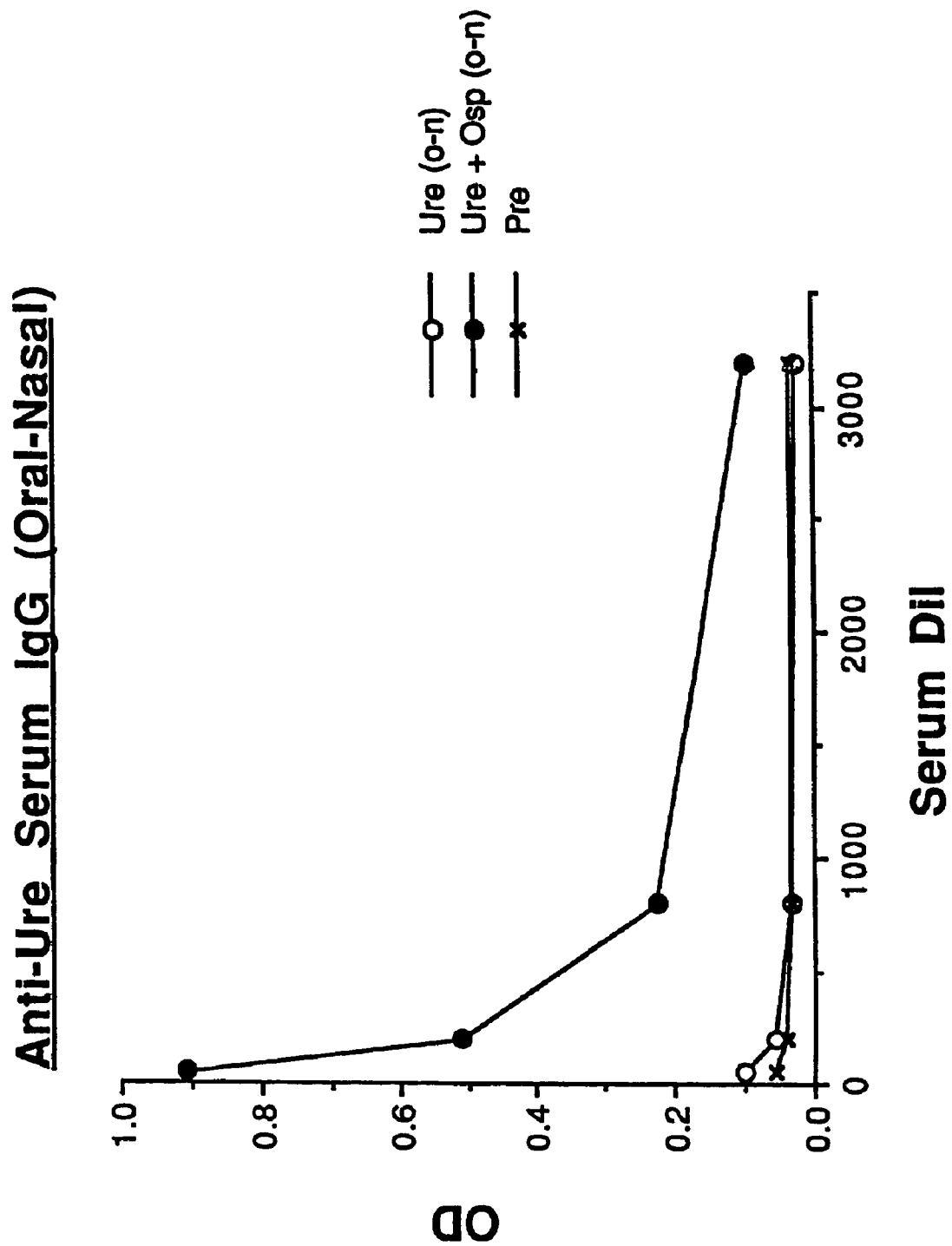
FIG. 4 is a graphical representation of the immune response of mice immunized twice, both intranasally and intragastrically, with either jack bean urease alone or both urease and OspA, as measured in an anti-urease ELISA at day 9 after the second immunization.
Figure 5:
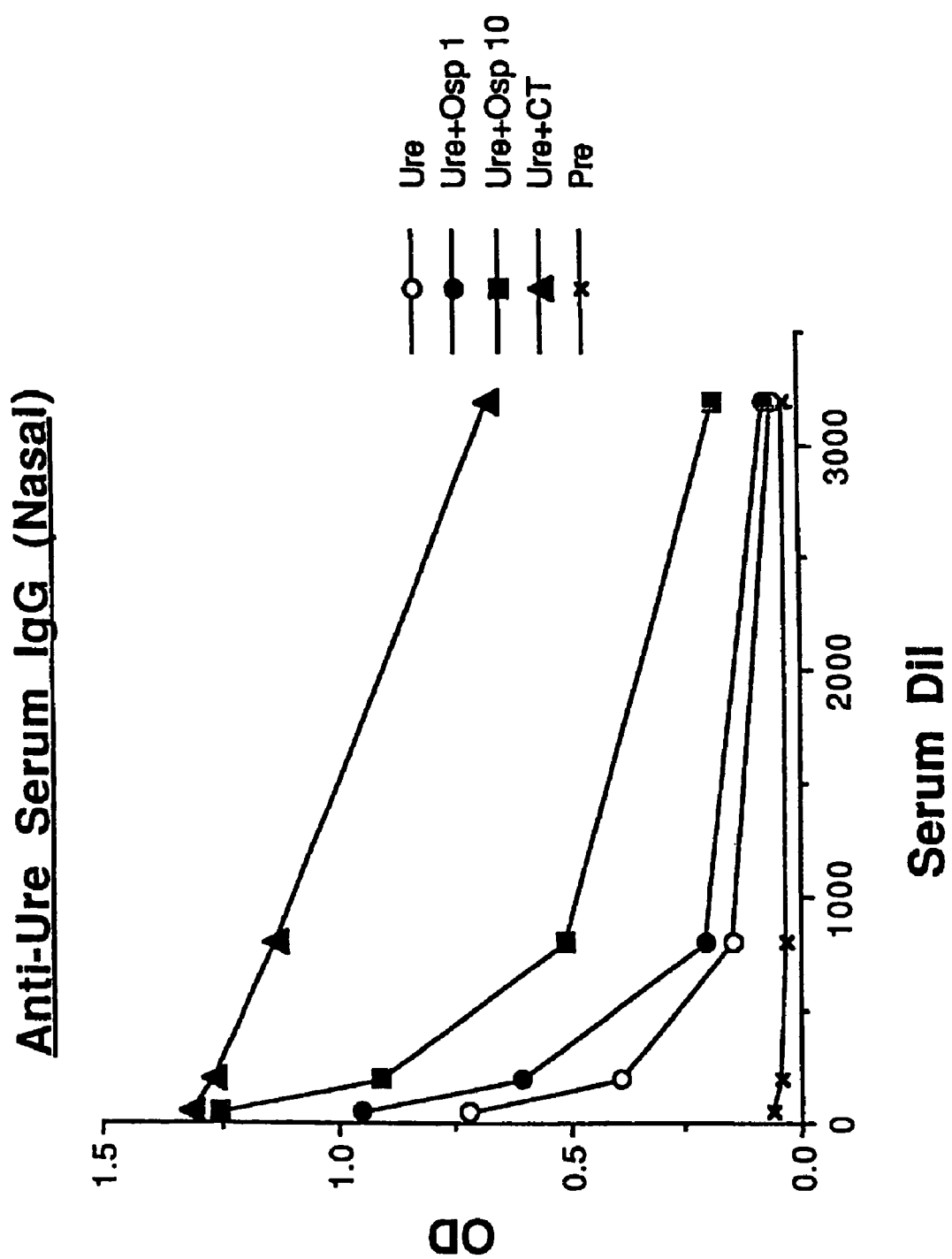
FIG. 5 is a graphical representation of the immune response of mice immunized twice, intranasally, with jack bean urease, either above or with OspA or cholera toxin, as measured in an anti-urease ELISA at day 9 after the second immunization.

The following day, plates were washed 4× with PBS/0.05% Tween 20 and blocked with PBS with 1% BSA for 30 min. at room temperature. After another wash, each well received 100 μl of PBS with 0.05% Tween 20 and 0.1% BSA (PBS/T/B). Sera were pooled within each group of mice and serially diluted, and plates were incubated for 3 hr. at room temperature. After washing, 2° antibody biotinylated goat-antimouse IgG or IgA (Amersham) diluted 1:5,000 in PBS/T/B was added, and plates were incubated for two hours at room temperature. Plates were washed again and incubated with streptavidin horseradish peroxidase (Amersham) diluted 1:2,000 in PBS/T/B for 1.5 hr. at room temperature. After a final wash the substrate, OPD (Sigma), was added and plates were incubated 10–20 min. Finally, the reaction was stopped with 50 μl 2 N $H_2SO_4$ and plates were read at 490/650 nm with a Molecular Devices plate reader. The results shown in FIGS. 3, 4 and 5 demonstrate that lipidated OspA, but not non-lipidated OspA, administered mucosally induces a very strong serum IgG response. Additionally, lipidated OspA had a strong adjuvant effect on the serum IgG response to urease.

Having thus described in detail certain preferred embodiments of the present invention, it is to be understood that the invention defined by the appended claims is not to be limited by particular details set forth in the above description, as many apparent variations thereof are possible without departing from the spirit or scope thereof.

What is claimed is:

1. A method for inducing an immunological response in a host comprising the steps of:
    administering to the host at least one antigen, wherein the at least one antigen is an influenza antigen; and
    administering to the host a lipoprotein, wherein the lipoprotein is an expression product of a hybrid nucleic acid molecule, comprising a first nucleic acid sequence encoding a signal sequence of an OspA protein of *Borrelia* and a second nucleic acid sequence encoding a S. pneumoniae PspA protein, or fragment of the PspA protein comprising amino acids 1 to 314 thereof, wherein the sequences are contiguous.

2. The method of claim 1 wherein the antigen and the lipoprotein are administered simultaneously.

3. The method of claim 1 wherein, in the hybrid nucleic acid molecule, the first nucleic acid sequence and the second nucleic acid sequence are coupled in a translational open reading frame relationship.

4. The method of claim 1, wherein the antigen is an HA antigen.

5. The method of claim 1 wherein the lipoprotein is antigenic.

6. The method of claim 1 wherein the antigen and lipoprotein are administered mucosally.

7. The method of claim 6 wherein the antigen and lipoprotein are administered intranasally.

8. The method of claim 6 wherein the antigen and lipoprotein are administered intragastrically.

9. The method of claim 6 wherein the antigen and lipoprotein are administered both intranasally and intragastrically.

10. The method of claim 1 wherein the immunological response is therapeutic.

11. The method of claim 1 wherein the immunological response is prophylactic.

* * * * *